United States Patent [19]
Baugh

[11] Patent Number: 5,935,516
[45] Date of Patent: Aug. 10, 1999

[54] CLOSED ECOLOGICAL SYSTEM AND METHOD FOR SUPPORTING LIFE

[76] Inventor: Carl E. Baugh, P.O. Box 309, Glen Rose, Tex. 76043

[21] Appl. No.: 08/910,843

[22] Filed: Aug. 13, 1997

Related U.S. Application Data

[63] Continuation of application No. 08/524,397, Sep. 6, 1995, abandoned.

[51] Int. Cl.$^6$ .................................................. A61G 10/02
[52] U.S. Cl. .............................. 422/1; 422/104; 422/120; 128/205.26; 607/91; 600/14
[58] Field of Search .................................. 422/4, 120, 1, 422/104; 454/187, 188; 128/204.18, 205.26; 607/91; 600/13, 14

[56] References Cited

U.S. PATENT DOCUMENTS

| | | | |
|---|---|---|---|
| 1,827,530 | 10/1931 | Le Grand | 128/205.26 X |
| 3,367,308 | 2/1968 | Quattrone et al. | 600/21 X |
| 3,420,739 | 1/1969 | Bongers et al. | 435/42 |
| 3,547,118 | 12/1970 | Kolman | 128/205.26 |
| 3,587,574 | 6/1971 | Mercer | 128/205.26 |
| 3,658,051 | 4/1972 | MacLean . | |
| 3,678,337 | 7/1972 | Grauvogel . | |
| 4,569,836 | 2/1986 | Gordon | 424/1.37 |
| 4,620,538 | 11/1986 | Koegel et al. | 128/201.23 |
| 4,800,597 | 1/1989 | Healey | 4/599 |
| 4,811,729 | 3/1989 | Sands et al. | 128/202.12 |
| 4,876,773 | 10/1989 | Wade | 600/21 X |
| 4,893,615 | 1/1990 | Khabirova | 601/16 |
| 4,994,014 | 2/1991 | Gordon | 600/13 |
| 5,010,777 | 4/1991 | Yehl et al. | 454/187 X |
| 5,075,823 | 12/1991 | Chomyn | 362/2 |
| 5,087,438 | 2/1992 | Gordon | 424/489 |
| 5,109,837 | 5/1992 | Gamow | 128/202.12 |
| 5,183,456 | 2/1993 | Libofff et al. | 600/9 |
| 5,188,099 | 2/1993 | Todeschini et al. | 128/205.26 |
| 5,192,263 | 3/1993 | Kraus | 600/14 |
| 5,211,622 | 5/1993 | Liboff et al. | 600/9 |
| 5,224,922 | 7/1993 | Kurtz | 600/13 |
| 5,259,553 | 11/1993 | Shyu | 236/49.3 |
| 5,263,476 | 11/1993 | Henson | 128/204.18 |
| 5,267,939 | 12/1993 | Liboff et al. | 600/13 |
| 5,269,746 | 12/1993 | Jacobson | 600/13 |
| 5,360,001 | 11/1994 | Brill et al. | 128/205.26 |
| 5,368,544 | 11/1994 | Tran et al. | 600/9 |

Primary Examiner—Elizabeth McKane
Attorney, Agent, or Firm—Oldham & Oldham Co., L.P.A.

[57] ABSTRACT

An apparatus to contain a closed ecological system, wherein the apparatus includes a closed, air-tight chamber to contain an atmosphere. The chamber includes at least one access opening designed to allow plants, animals, raw materials, and other items to be placed within the chamber. The chamber includes a system for introducing oxygen and/or carbon dioxide into the chamber and for maintaining the oxygen and/or carbon dioxide at a predetermined concentration percentage of the atmosphere. Preferably, the closed ecological system of the present invention also includes a system for establishing a magnetic field within the chamber of a predetermined strength and orientation. The chamber may also include systems for elevating the atmospheric pressure within the chamber and for maintaining the atmosphere within the chamber at a predetermined temperature and humidity level. The chamber may also include a specialized lighting and sound system to establish light and sound of a predetermined intensity, frequency, and wavelength within the chamber. A satellite chamber may be provided in selective fluid communication with the closed ecological system for providing plants, animals, or chemical processes with short-term exposure to the conditions of the closed ecological system. The present invention is also directed to a method of establishing and maintaining a closed ecological system to support plant and animal life and to aid in the development, discovery, and/or production of new and improved chemical compounds that may be used as pharmaceuticals and other chemical compounds.

28 Claims, 6 Drawing Sheets

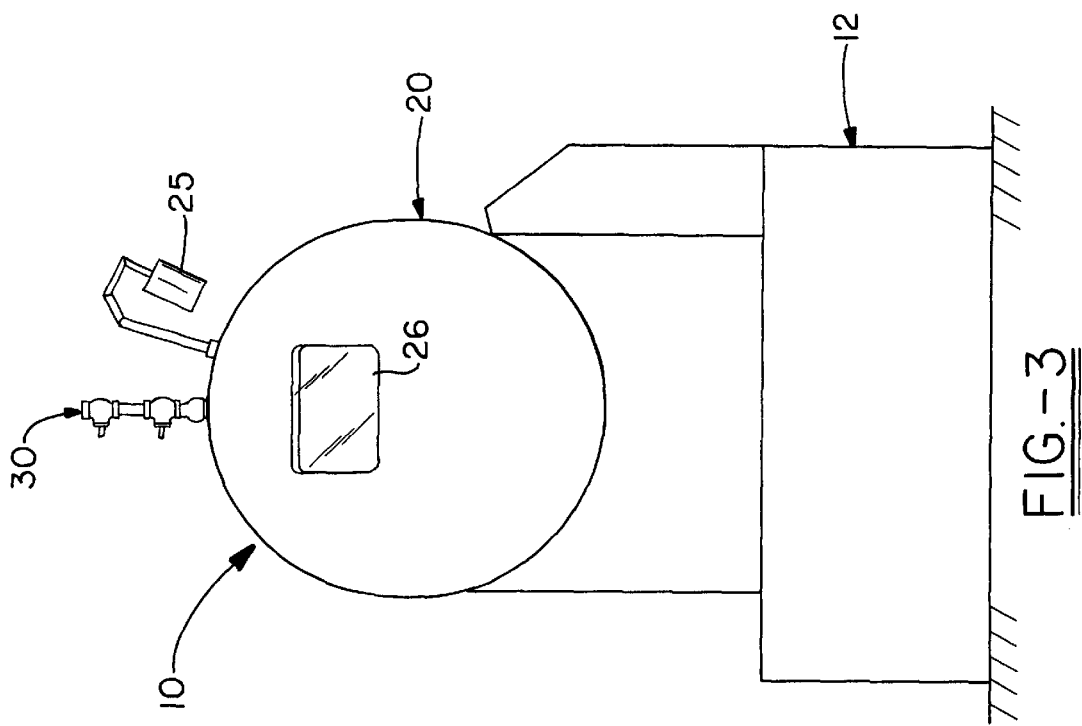
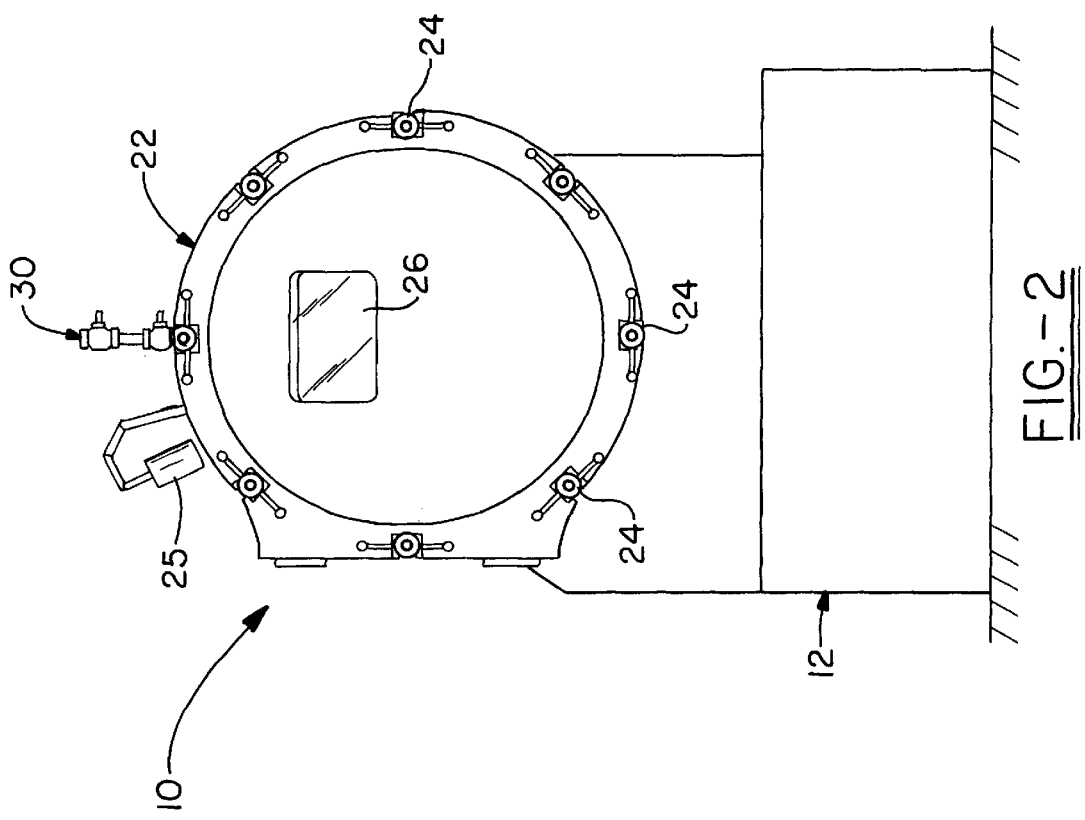

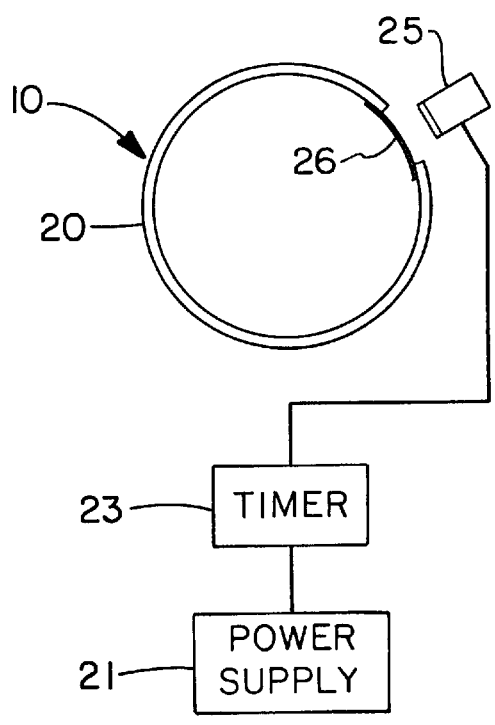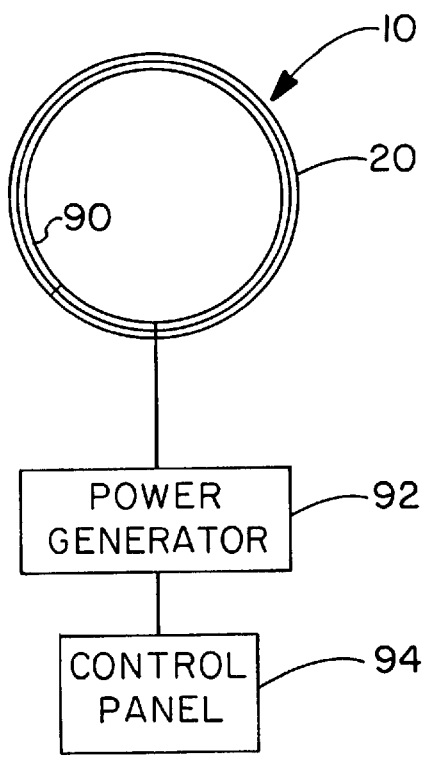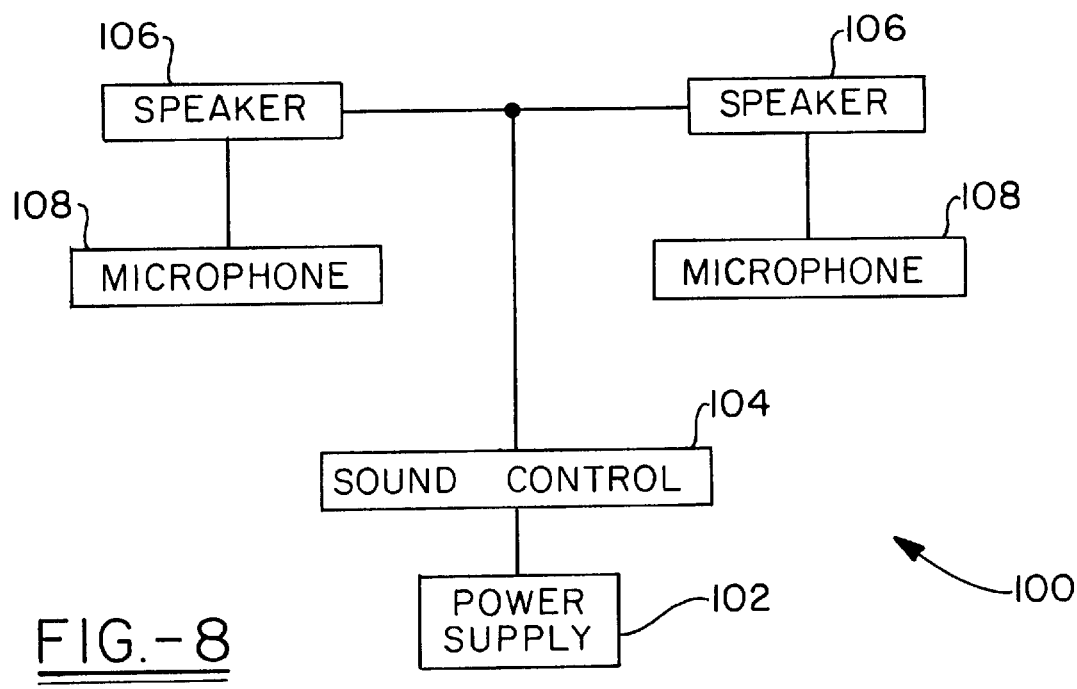

CLOSED ECOLOGICAL SYSTEM AND METHOD FOR SUPPORTING LIFE

This application is a continuation of application Ser. No. 08/524,397 filed Sep. 6, 1995, now abandoned.

FIELD OF INVENTION

The present invention relates generally to closed ecological systems, and more particularly to a method and apparatus for establishing and maintaining a closed ecological system wherein the environment within the closed system is controlled such that plant and animal life can exist to its more optimal potential and thrive, the effects and causes of plant and animal disease can be reduced and/or eliminated, mental well being of animals can be fostered, and new and improved pharmaceuticals and other chemical compounds (organic and inorganic) can be discovered and/or synthesized.

BACKGROUND OF THE INVENTION

The environment in which we live with plants and other animals has changed since biological systems first appeared. The composition of the air we breathe has continued to change. For example, there is reason to believe that the concentration of oxygen found within the air has decreased over time. The climate, including temperature, humidity, rainfall, snowfall, and the like has also been changing. It is further theorized that other important changes in the environment of the earth over time have been the marked decrease in atmospheric pressure, a decrease in the concentration of carbon dioxide in the earth's atmosphere, changes in the strength and orientation of the earth's magnetic field, and the change in the intensity and characteristics of the light radiation to which we are exposed. Furthermore, sounds of nature such as singing birds have become increasingly difficult to encounter due to a general decrease in the population of songbirds.

Many of the above and other changes are a natural result of the maturing of the earth. Other changes to the earth's environment are caused by purely natural events—volcanic eruptions, earthquakes, tidal waves, glaciers, and the like alter the earth itself and the surrounding atmosphere. Other changes to the earth and its atmosphere are due entirely to man. Pollution, overpopulation, overdevelopment, overutilization of natural resources, fishing, hunting, and farming have all altered our world. As the human population continues to increase, the pace at which these changes occur will inevitably increase.

These changes in the earth and the surrounding environment have had a detrimental impact on plants and animals including man. Certain plants and animals have vanished from the earth, unable to adapt to the changed earth. Many of the remaining varieties of plants and animals have found it difficult to thrive. The fruits and vegetables of trees and plants have lost taste and nutritional value. Animals, including humans, are increasingly disease stricken, weak, and otherwise unhealthy. Humans seem to have lost their general sense of well being, leading to an increase in depression, suicides, crime, violence, sickness, and other social and physical ailments and have become increasingly lethargic with shortened attention spans.

The increasing physical and mental ailments of humans has led to a constant search for new and improved pharmaceuticals to combat these sicknesses. As one example, scientists are constantly searching the far reaches of the planet for naturally occurring antiviral and antibiotic substances. Once such naturally occurring substances are discovered, scientists may attempt to synthesize these drugs in a laboratory. While much progress has been made in the field of locating and synthesizing these compounds for use as pharmaceuticals, many ailments currently have no known effective treatment drugs or the causative agents have been able to adapt or modify their own structure to develop a resistance to such treatments. For example, many cancers and AIDS have been particularly resistant to pharmaceuticals located and/or synthesized using conventional methods in standard environmental conditions. It is believed that the changes in the earth's environment have prevented certain drugs from being created in nature, discovered, and/or synthesized, and has prevented the compounding of certain organic and inorganic elements.

SUMMARY OF THE INVENTION

It is therefore an object of the present invention to solve the above and other problems caused by changes in the earth and its surrounding environment.

It is also an object of the present invention to provide a closed ecological system including an atmosphere with an elevated oxygen content.

It is another object of the present invention to provide a closed ecological system including an atmosphere with an elevated atmospheric pressure.

It is another object of the present invention to provide a closed ecological system with an atmosphere having an elevated concentration of carbon dioxide.

It is a further object of the present invention to provide a closed ecological system including a low level magnetic field.

Yet another object of the present invention is to provide a closed ecological system including specialized lighting and sound.

Still a further object of the present invention is to provide a closed ecological system with a controlled temperature, humidity, and other climate variables.

Another object of the present invention is to provide a closed ecological system having an overall environment that is favorable to the natural formation and/or the manufacture of improved compounds used to manufacture pharmaceuticals for the treatment of sickness and disease.

The present invention accomplishes these and other objects by providing an apparatus to contain a closed ecological system, wherein the apparatus comprises a closed, air-tight chamber to contain an atmosphere, and wherein the chamber includes at least one access opening. The access opening is designed to allow plants, animals, raw materials, and other items to be placed within the chamber. The chamber includes means for introducing oxygen and/or carbon dioxide into the chamber and means for maintaining the oxygen and/or carbon dioxide at a predetermined concentration percentage of the atmosphere. Preferably, the closed ecological system of the present invention also includes means for establishing a magnetic field within the chamber of a predetermined strength and orientation. The chamber may also include means for elevating the atmospheric pressure within the chamber and means for maintaining the atmosphere within the chamber at a predetermined temperature and humidity level. The chamber may also include a specialized lighting and sound system to establish light and sound of a predetermined intensity, frequency, and wavelength within the chamber. A satellite chamber may be provided in selective fluid communication with the closed ecological system for providing plants, animals, or chemical processes with short-term exposure to the conditions of the closed ecological system.

The present invention is also directed to a method of establishing and maintaining a closed ecological system to support plant and animal life and to aid in the development, discovery, and/or production of new and improved chemical compounds that may be used as pharmaceuticals.

BRIEF DESCRIPTION OF THE DRAWINGS

FIG. 2 is a side elevational view of a closed ecological system in accordance with the present invention;

FIG. 3 is a side elevational view of a closed ecological system in accordance with the present invention;

FIG. 6 is a schematic representation of a closed ecological system including a lighting system in accordance with the present invention;

FIG. 7 is a schematic view of a closed ecological system including a magnetic field generation system in accordance with the present invention;

FIG. 8 is a schematic view of an audio system for use with a closed ecological system in accordance with the present invention;

DETAILED DESCRIPTION OF THE INVENTION

Figure 1:
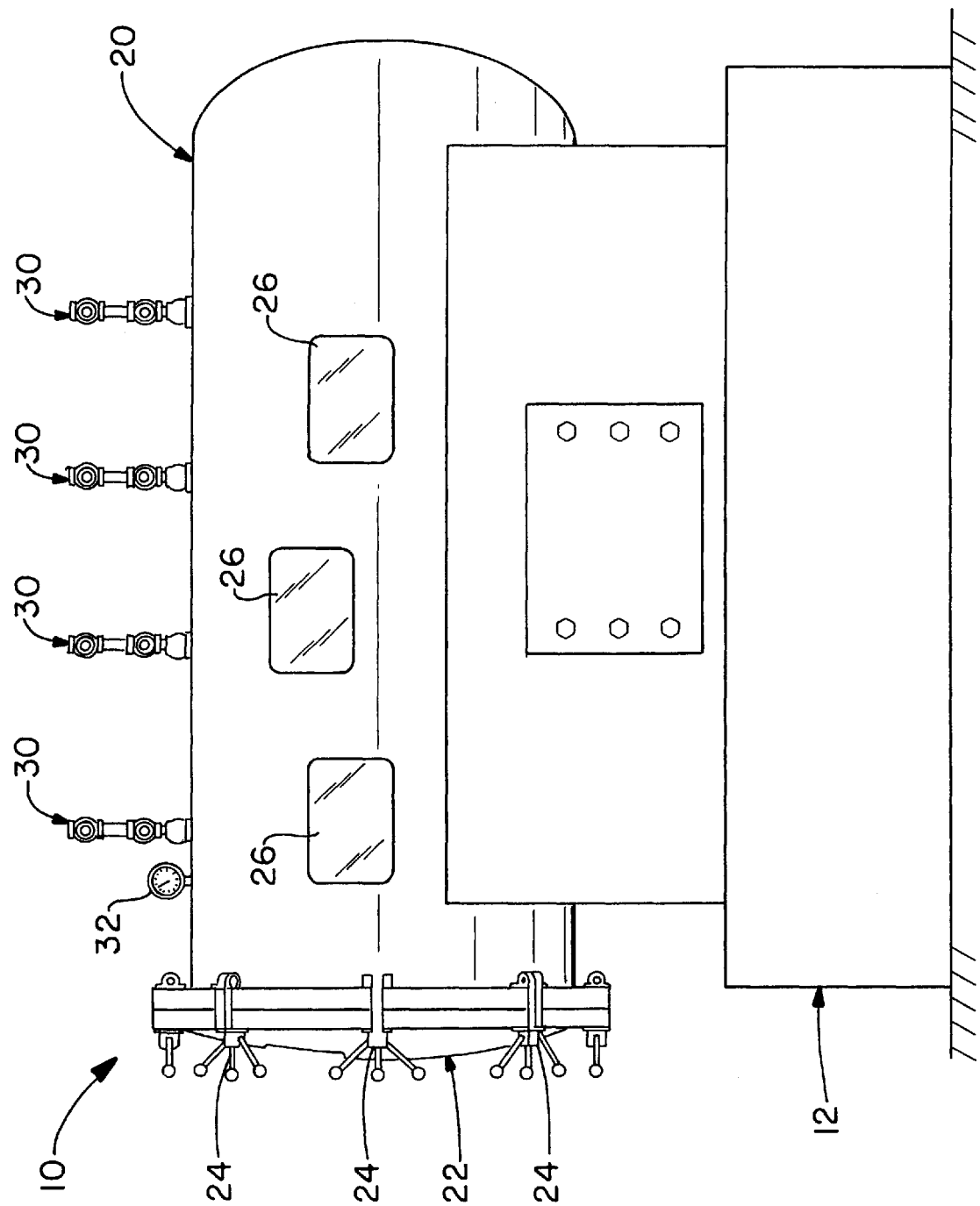
FIG. 1 is a front elevational view of a closed ecological system in accordance with the present invention.
Figure 4:
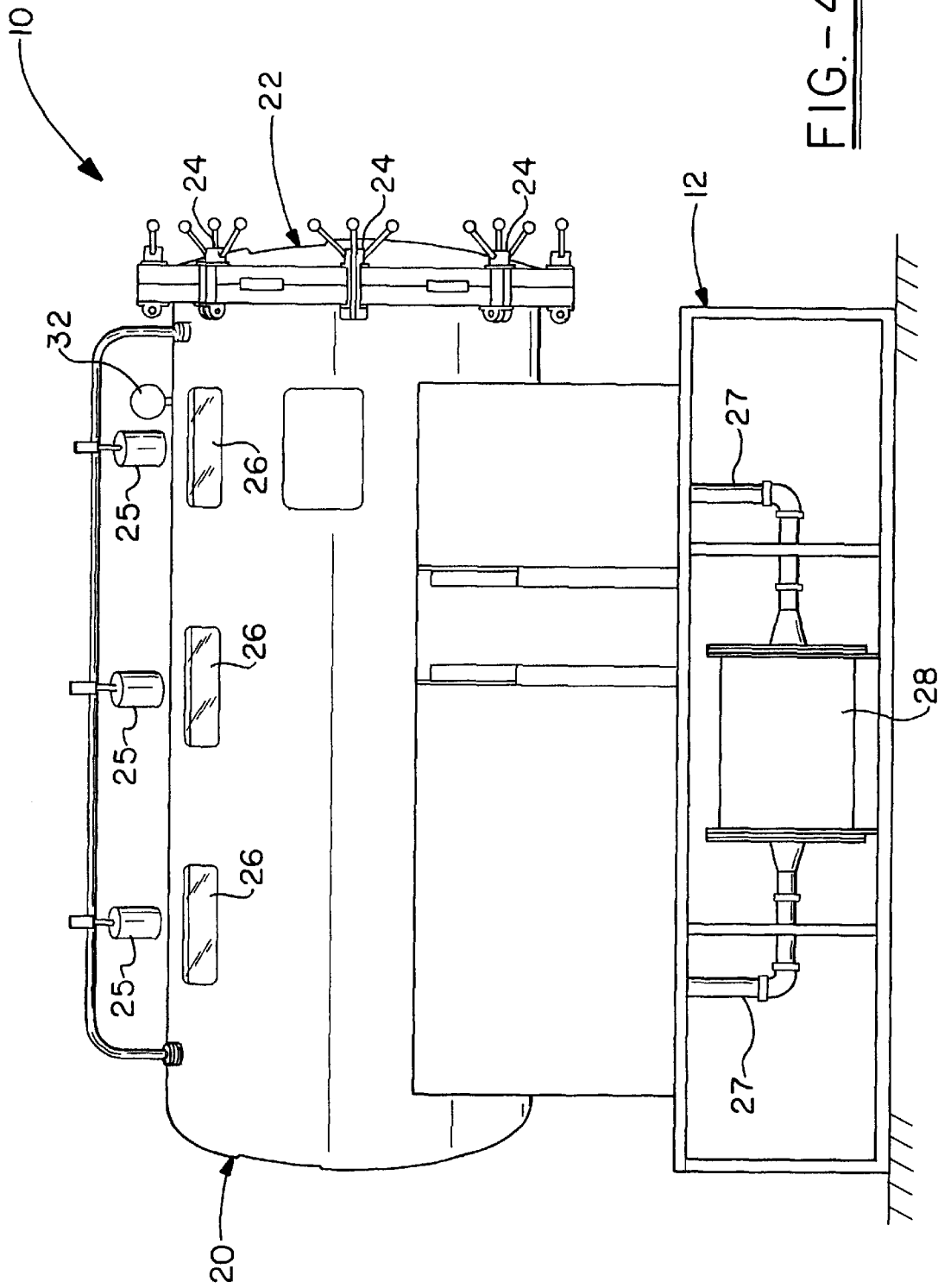
FIG. 4 is a rear elevational view of a closed ecological system in accordance with the present invention.

Reference will now be made in detail to the present preferred embodiments of the invention, examples of which are illustrated in the accompanying drawings. Wherever possible, the same reference numbers will be used throughout the drawings to refer to the same or like parts.

An apparatus for establishing, containing, and maintaining a closed ecological system in accordance with the present invention is shown generally at 10 in FIGS. 1–7 and comprises an air-tight, substantially hollow chamber 20 made of plastic, metal, fiberglass, or any other suitable material. Chamber 20 includes a sealable access opening such as hinged door 22 provided with suitable air locks 24 and seals (not shown) to ensure that door 22 does not reduce the air-tight integrity of the chamber 20. Chamber 20 is designed to contain therein an atmosphere, plants, animals, objects and any other desired components of a closed ecological system such that plants and animals may live therein and such that chemical reactions such as the production of pharmaceuticals can be carried out therein. Chamber 20 may be of any size desired such that the ecological system established and maintained therein may be of any suitable size. Chamber 20 may only be large enough to contain a few small plants and animals, or chamber 20 may be large enough to contain a community of numerous human beings. As shown, chamber 20 is sufficiently large to contain at least one human being and several plants and animals. Chamber 20 may include air-tight windows 26 formed therein or in door 22 thereof using suitable glass or plastic to allow those outside of the chamber 20 to observe the plants, animals, and any other animals, objects and/or conditions inside of chamber 20. Door 22 may be opened to remove, add, or reorient specimens as desired, after depressurization has returned internal pressure to ambient conditions. Windows 26 are designed to filter ultra-violet (UV) light to prevent unwanted UV light from affecting the ecological system contained within chamber 20. Specifically, UV light causes or encourages the formation of "free radicals" that are thought to be harmful to animals.

Chamber 20 is supported upon a base 12 to prevent the unwanted movement of the chamber 20 and other components of the apparatus 10. A sub-chamber or premixing chamber 28 (FIGS. 4 and 5) is preferably provided and is in selective fluid communication with chamber 20 through pipes or other conduits 27. Sub-chamber 28 provides a means for premixing the gases and liquids to be added to chamber 20 to ensure that such gases and liquids are uniformly distributed within chamber 20. It should be recognized that chamber 28 may also function as a satellite chamber in selective fluid communication with chamber 20 for establishing and maintaining a closed ecological system similar to that found within chamber 20, such that plants, animals, chemical reactions and the like can be placed within the closed ecological system found within the satellite chamber for time periods that differ (usually shorter) from the amount of time chamber 20 needs to remain closed. To function as a satellite chamber, sub-chamber 28 would need to include an access opening such as a door, and would need to include at least some of the features of chamber 20 as they are set forth below. Also, if sub-chamber 28 is to be used as a satellite chamber, chamber 20 and sub-chamber must be shielded from each other with a lead shield or the like to prevent the magnetic field (discussed fully below) of one chamber 20, 28 from interfering with the magnetic field of the other chamber 20, 28. For example, in addition to conducting experiments relating to the natural creation and/or synthesis of pharmaceuticals within chamber 20, sub-chamber 28, when properly adapted as a satellite chamber, may alternatively be utilized for the same types of experiments. Various chemicals could be mixed and placed within sub-chamber 28 for a period of time, and thereafter be removed from sub-chamber 28 and examined, without opening door 22 of chamber 20 and without altering the ecological system found within chamber 20.

Conduits 27 between sub-chamber 28 and chamber 20 are selectively blocked or closed using gate valves 29 (FIG. 5) or the like so that sub-chamber 28 may be selectively "disconnected" or prevented from being in fluid communication with chamber 20 to protect the integrity of the ecological system found within chamber 20 during premixing operations. After sub-chamber 28 is "disconnected" from chamber 20, various gases and other components of the closed ecological system as described herein may be introduced into chamber 28, without altering the ecological system within chamber 20. When the gases and liquids introduced into sub-chamber 28 are properly mixed, which may occur naturally or with the aid of mixing devices such as blowers, gate valves 29 may be opened to allow the properly mixed gases and liquids to enter chamber 20 as is described below. Sub-chamber 28 includes a pressure relief valve 25 so that excess pressure may be vented from sub-chamber 28 if necessary. Those skilled in the art will recognize that the apparatus need not include a sub-chamber 28 and such is contemplated herein, although use of sub-chamber 28 is thought to be preferable. Also, those skilled in the art will recognize that any ecological system or conditions created and maintained in chamber 20 may also be created and maintained in sub-chamber 28, and for reasons of clarity, the following description will not necessarily refer to providing an ecological system within both chambers 20,28 but will instead refer primarily to chamber 20.

Apparatus 10 includes numerous components and features such that an ecological system can be created and maintained within chamber 20 and so that the characteristics of the ecological system so created and maintained, such as temperature, atmospheric pressure, humidity, magnetic field, oxygen level, carbon dioxide level, and the like may be accurately varied and monitored. One or more feeder valves such as dual ball valves 30 are provided in fluid communication with the interior of chamber 20 and are also connected to vacuum/pressure pump 38 (FIG. 5) to allow fluids such as air, oxygen, water, nutrients and others (organic and inorganic) to be communicated from the appropriate source into the ecological system found within chamber 20 through one or more valves 30. As is noted above, it is thought preferable to premix fluids in sub-chamber 28 prior to introducing the fluids into chamber 20. Feeder lines or conduits may be surrounded by a coolant or other thermal fluid to vary the temperature of the fluid in the feeder line. Because of the potentially elevated atmospheric pressure (hyperbaric pressure) within chamber 20, dual ball valves 30 are thought to provide a more effective seal to prevent the escape of gases from the chamber 20 and to otherwise protect the integrity of the closed ecological system created and maintained by the apparatus 10, although other suitable valves are known and are contemplated for use in conjunction with the present invention 10. A pressure gauge 32 is also provided to allow those outside of chamber 20 to monitor the atmospheric pressure within chamber 20.

Figure 5:
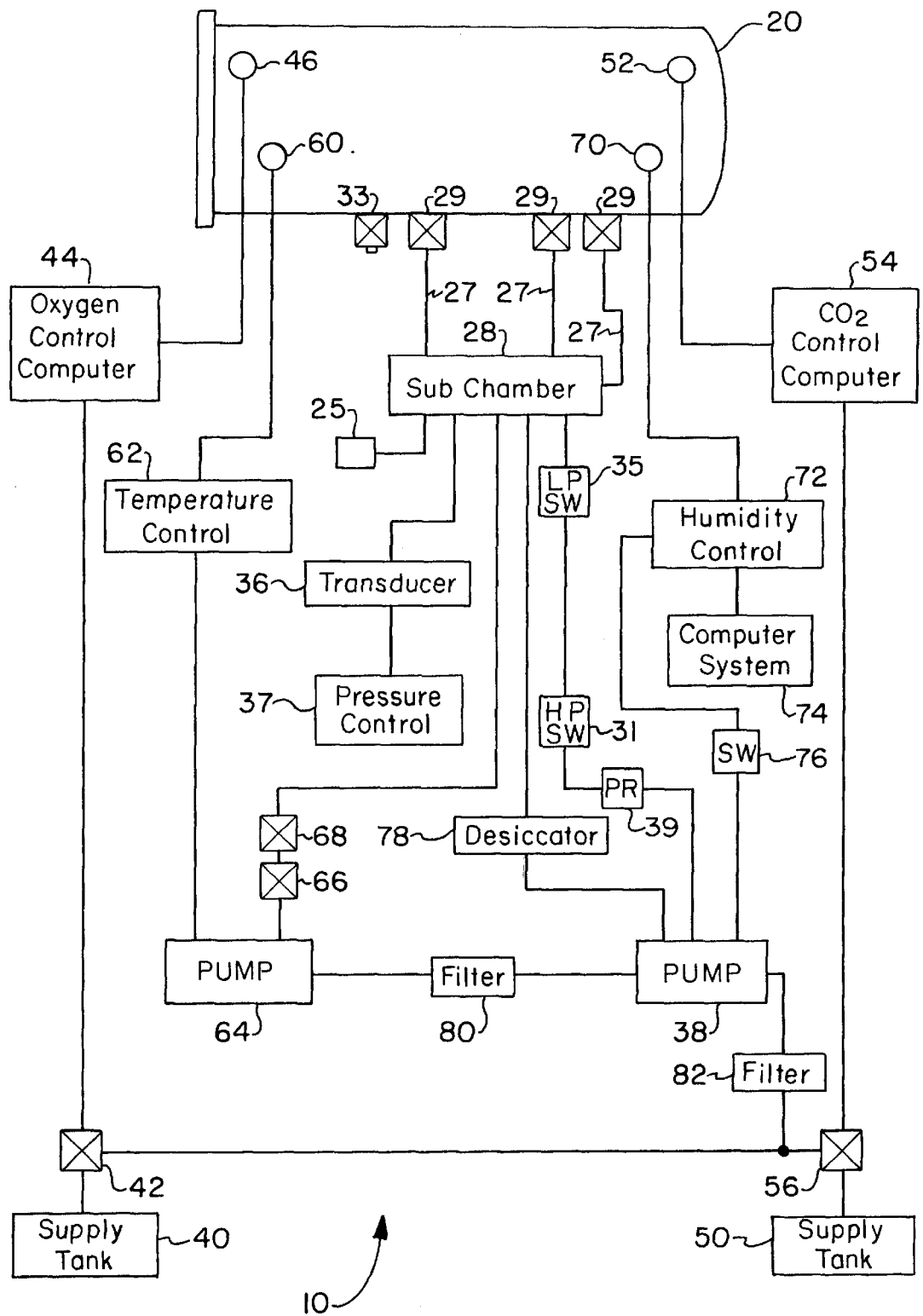
FIG. 5 is a schematic representation of a closed ecological system in accordance with the present invention.

The pressure of the atmosphere within chamber 20 may be varied as desired to provide an elevated atmospheric pressure. It is thought preferable for example to create a hyperbaric closed ecological system—i.e., a closed ecological system having an increased atmospheric pressure relative to the atmospheric pressure normally encountered on earth. It is thought most preferable to provide an environment inside of chamber 20 having an atmospheric pressure of 1 to 2 atmospheres of pressure. FIG. 5 shows a pressure sensor or transducer 36 coupled to a pressure control mechanism such as pressure control computer 37 to control and regulate the pressure inside of chamber 20 and/or 28. Transducer 36 converts air pressure into electrical signals to provide input data to pressure control computer 37 so that computer can continually monitor the air pressure within chamber 20 and adjust the same accordingly. A vacuum/pressure pump 38 is provided in fluid communication with chamber 20 so that the pressure in chamber 20 can be elevated using compressed air generated by pump 38 and transferred into chamber 20 through one or more of the valves 30. Pump 38 may also be used to create a vacuum suction to draw air from chamber 20 resulting in a low pressure environment within chamber 20. As a safety and control measure, a high pressure safety switch 35 is provided to prevent overpressurization of the chamber 20. Likewise, a low pressure safety switch 31 is provided to prevent an excessive vacuum condition from being established within chamber 20. A pressure relay 39 is provided to selectively energize vacuum/pressure pump 38 as needed to increase or decrease the atmospheric pressure in chamber 20 and a blow off valve 33 is provided in fluid communication with chamber 20 to allow excessive air pressure that may be contained therein to be rapidly vented automatically when the atmospheric pressure within chamber 20 exceeds some threshold value such as 2 atmospheres.

In addition to an elevated atmospheric pressure, the closed ecological system of the present invention 10 preferably includes an atmosphere within chamber 20 having an elevated oxygen concentration relative to the concentration of oxygen normally found in the air surrounding the earth. Specifically, it is thought preferable to maintain a concentration of oxygen within chamber 20 such that the oxygen is equal to 22%–30% by volume of the atmosphere contained within chamber 20 when the atmospheric pressure is in the range of 1–2 atmospheres. For long term occupation within chamber 20 the oxygen level is most preferably maintained at 22%–24% by volume at 2 atmospheres of pressure, while for short term occupation, a month or less, the oxygen level within chamber 20 may be elevated to 26%–30% by volume at 2 atmospheres of pressure.

A source of oxygen such as a pressurized holding tank 40 or the like is provided to supply oxygen to the system 10. Alternatively, oxygen may be generated by an electrolysis process. Oxygen supply tank 40 is in fluid communication with vacuum/pressure pump 38 and chamber 20 using the appropriate conduits and connections. A valve assembly such as oxygen solenoid valve 42 is controlled by a control mechanism such as oxygen control computer 44 which is provided between supply tank 40 and pump 38 to regulate the flow of oxygen to pump 38 and into chamber 20 through one or more valves 30 (FIG. 1). An oxygen sensor 46 is provided in one or both chambers 20, 28 to sense the concentration of oxygen therein. Sensor 46 provides the concentration to oxygen control computer 44 as input so that computer 44 may determine if oxygen solenoid valve 42 should remain closed or should be opened to allow more oxygen to enter chambers 20, 28. A filter 82 is preferably provided between oxygen supply tank 40 and pump 38 to filter any contaminants from the oxygen.

Figure 9:
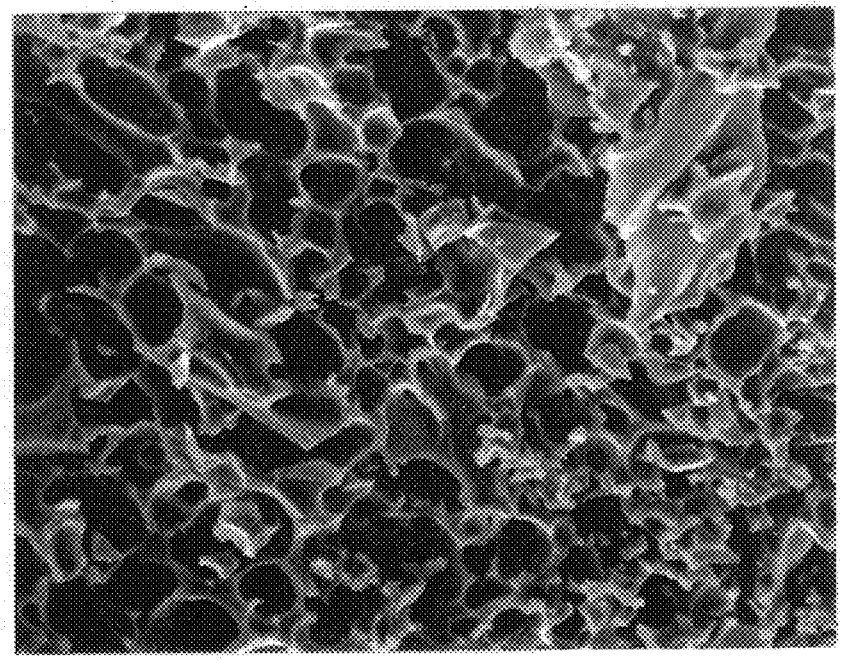
FIG. 9 is a scanning electron microscope view of Copperhead snake venom taken from a Copperhead snake living under normal, ambient conditions on earth.
Figure 10:
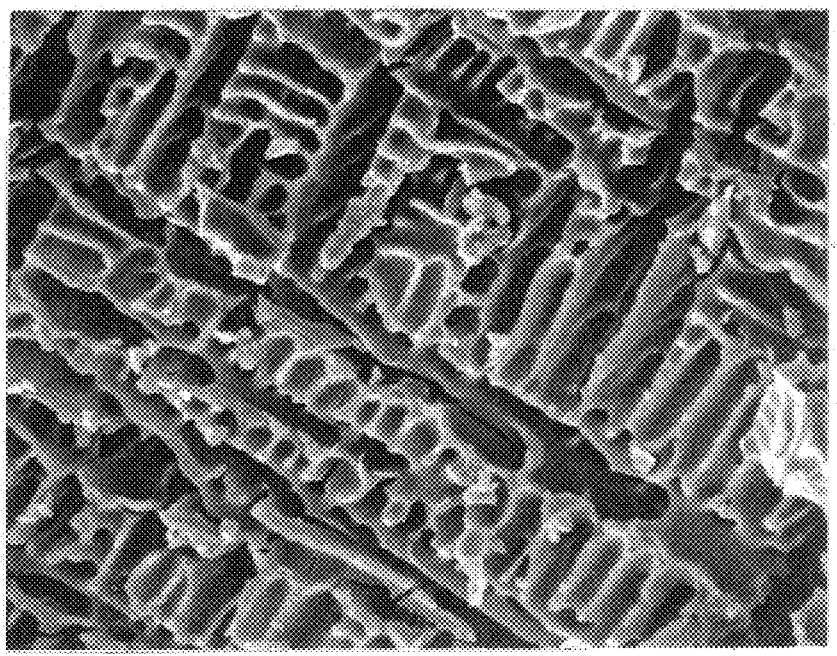
FIG. 10 is a scanning electron microscope view of Copperhead snake venom taken from a Copperhead snake that lived for four weeks in a closed ecological system in accordance with the present invention.

By combining an increased level of oxygen concentration with a hyperbaric atmospheric pressure inside of chamber 20, the amount of oxygen absorbed by animals within the chamber 20 is maximized. This increased absorption of oxygen by the animals, including humans, leads to increased physical healing through the increased oxygen absorption of the cells of the animal, increased immunity, an increased level of mental awareness, and a general sense of well being for the animals that spend time within the closed ecological system created and maintained by apparatus 10. The increased absorption of oxygen by the animal cells raises the internal temperature of the cells, resulting in the damage to cancerous cells which have been found to have a lower resistance to heat than ordinary cells. As is discussed below in relation to FIGS. 9 and 10, the increased concentration of oxygen combined with an elevated atmospheric pressure, alone or in combination with other aspects of the closed ecological system found within chamber 20, has been found to result in the natural production of a superior snake venom having medicinal properties. Also, it is believed that the in increased oxygen level and atmospheric pressure contributes to improving the reactions among various chemicals which can lead to the production of superior chemical compounds such as very effective pharmaceuticals that may be used to treat illnesses for which there are currently few or no effective treatment drugs.

In conjunction with increasing the concentration of oxygen in chamber 20, it may also be desirable in certain circumstances to increase the concentration of carbon dioxide ($CO_2$) in chamber 20. It has been theorized that an increased concentration of carbon dioxide lengthens the gestation period for mammals. This may be desirable to prevent premature births (births before the end of the normal gestation period for any particular mammal) or to lengthen the gestation period beyond normal to increase the development of the fetus. Carbon dioxide normally comprises approximately 0.026% by volume of the air normally encountered by mammals on earth. The apparatus 10 allows a closed ecological system to be created wherein the concentration of carbon dioxide therein may be elevated to approximately 0.1%–0.3% by volume. This increased level of carbon dioxide, in conjunction with an elevated atmospheric pressure of approximately 2 atmospheres leads to the lengthened gestation period for mammals. It has also been found that raising the level of carbon dioxide assimilation in plants enhances plant production of stalks, leaves, and fruit.

As is shown in FIG. 5, a supply of carbon dioxide such as a pressurized carbon dioxide supply tank 50 or the like is provided in fluid communication with pump 38, through filter 82 designed to remove contaminants from the carbon dioxide. Pump 38 is in fluid communication with chamber 20 through one or more dual ball valves 30. A carbon dioxide sensor 52 is capable of sensing the concentration of carbon dioxide in the chambers 20, 28. A control mechanism such as carbon dioxide control computer 54 receives the concentration of carbon dioxide from sensor 52 as input and determines whether to increase the concentration thereof. If more carbon dioxide is needed within chamber 20, carbon dioxide control computer 54 causes a valve assembly such as carbon dioxide solenoid valve 56 to open, thereby allowing carbon dioxide to flow from supply tank 50 to pump 38 and thereafter into chamber 20 through one or more valves 30.

The apparatus 10 of the present invention also includes systems to control the temperature and humidity of the air within chamber 20 and also includes an air filtration system to remove contaminants from the air. A temperature sensor 60 is provided within chamber 20 to sense the temperature therein. Sensor 60 is coupled to a temperature control unit 62 which may be a computer or a simple thermostat, which is coupled to a heating and cooling pump 64. Heating and cooling pump 64 is capable of adding heat to or removing heat from chambers 20, 28 as desired to control the temperature therein. Heating and cooling pump 64 is coupled to chambers 20,28 through a check valve 68 to sub-chamber 28 and main chamber 20. Preferably, the temperature inside of chambers 20 and 28 is maintained in the range of 70°–80° Fahrenheit (F.) at all times. The temperature may be decreased to approximately 70° F. at "night" and maintained at approximately 80° F. during the "day." Of course, the terms "day" and "night" do not necessarily refer to the time of day outside of the chambers 20, 28 although "day" and "night" within the chambers 20, 28 may be controlled to correspond to conditions outside of the chambers 20, 28. Electric lights 25 (FIGS. 4 and 6) are provided to shine light into the chamber 20 through windows 26. Lights 25 receive power from a power supply 21 and are also connected to a control box/timer 23 that allows an operator of the apparatus 10 to vary the intensity, duration, and wavelength of each light 25. Lights 25 are preferably filtered to provide a wavelength primarily in the range of 6365 Angstroms which results in a magenta light. Therefore, "day" may occur anytime lights 25 are on while "night" may occur anytime no light is shining through windows 26 because of darkness surrounding chamber 20 or because of shades or the like being placed over windows 26.

The humidity within chambers 20, 28 is also closely monitored and is maintained in the range of 40%–60%. A humidity sensor 70 is provided within chamber 20 to sense the percentage of moisture found in the atmosphere within chamber 20 and is coupled to a humidity control unit 72 which may include a gravity collection/injection valve apparatus or any other suitable humidity control apparatus. Humidity control unit 72 is coupled to a computer system 74 that is capable of controlling the humidity control unit 72 to maintain the humidity within chambers 20, 28 at the desired 40%–60%. Humidity control unit 72 and computer system 74 are coupled through a switch 76 to vacuum/pressure pump 38 such that pump 38 may be selectively energized through switch 76. Pump 38 is coupled to a desiccator unit 78 which is in fluid communication with chambers 20, 28. Upon being energized through switch 76, pump draws air from within chambers 20, 28, through desiccator unit 78 wherein moisture is removed from the air. The dehumidified air is then returned into chamber 20 through one or more valves 30. Because of the closed nature of closed ecological system created and maintained in apparatus 10, it will not normally be necessary to add humidity to chambers 20, 28, although such is contemplated and may be accomplished by the addition of a humidifier to the apparatus 10.

Apparatus 10 is also provided with an air filtration system comprising an air filter 80 provided in fluid communication with vacuum/pressure pump 38 and heating and cooling pump 64 such that any air introduced into chambers 20, 28 using vacuum/pressure pump 38 and/or heating and cooling pump 64 is first filtered of any airborne contaminants such as dust and bacteria. Both filter 80, and filter 82 discussed previously, may be a conventional filter media such as a foam or mesh, may be an electrostatic ionization filtration system that electrically charges the contaminants so that they are attracted to either a positively charged or negatively charged surface, or the air filters 80,82 may be a combination thereof or any other suitable air filtering system.

The apparatus 10 further comprises means for establishing and maintaining a magnetic field within the chamber 20 of a predetermined strength and orientation. As with other aspects of the apparatus and the closed ecological system created and maintained thereby, a magnetic field may also be established within chamber 28 although for reasons of clarity, reference will only be made to chamber 20. Referring to FIG. 7 wherein the apparatus 10 is shown schematically, a magnetic field coil 90 comprising shielded copper wire or the like surrounds and/or lines chamber 20 and is coupled by wires or the like to a D/D power generator 92 which generates controlled electromagnetic pulses (Hz) at optimal energy levels (Gauss). D/D power generator 92 is connected to a control mechanism such as control panel 94 which may be an analog device or a digital computer allowing a machine operator to vary the strength and orientation of the magnetic field created by the magnetic field coil 90 by varying the magnitude and direction of the electric current flowing through magnetic field coil 90.

It is thought preferable to establish and maintain a magnetic field within chamber 20 of 0.5 Hz to 30 Hz at 1–5 Gauss and is thought most preferable to average a magnetic field of 8 Hz within chamber 20. A variable magnetic field of 8 Hz (average, with intensity nearing 5 Gauss) is thought to simulate the magnetic field found on earth thousands of years ago. The magnetic field may be cyclical—i.e., turned on and off, or raised and lowered depending upon other aspects of the closed ecological system. For example, the magnetic field may be elevated only in the "day" or "night" as such terms are defined above. Alternatively or in conjunction with the "day and "night" variables, the magnetic field may be dependent upon the song activity of live birds present within the chamber 20 or dependent upon the sounds of birds that are broadcast within the chamber 20 through a sound system as is discussed in greater detail below.

FIG. 8 schematically illustrates a sound system 100 to be used in conjunction with the apparatus 10 of the present invention to establish predetermined sounds within the chamber 20. Sound system 100 comprises a power supply 102 which may be the same as power supply 21 discussed previously, or power supply 102 may be separate therefrom. Power supply 102 is connected to and provides electrical power to a sound control panel 104 from where one may control the selection and characteristics of the sounds broadcast by the sound system 100 into chamber 20. Control panel 104 is connected to one or more speakers 106 for broadcasting sound and is also connected to one or more microphones 108 for receiving sound from within chamber 20 and transmitting the same onto a recording medium or for broadcasting such sounds outside of chamber 20. Control panel 104 may be located either inside or outside of chamber 20 such that sound system 100 may be controlled by a person outside of chamber 20 or inside chamber 20, depending upon the location of control panel 104. It has been found beneficial for animals and plants to be within chamber 20 while sound from sound system 100 is broadcast into chamber 20. For example, harmonic music corresponding to songs of birds within chamber 20 at controlled times and under controlled conditions has been found to be particularly beneficial to plants and animals within chamber 20. By broadcasting the songs of birds where the songs are tuned to a frequency of 256 Hz ranging from 2–60 decibels in intensity, the sounds of the harmonic music will be tuned to the antenna of the DNA and cellular structure of the cells of animals which thereby causes a resonance of such cells and alters the vibratory cycle of the cells, leading to the improved health thereof, and leading to the deterioration of abnormal cells. As an alternative to broadcasting songs of birds into chamber 20, symphonic music, broadcast into chamber 20 in accordance with the above-noted broadcast parameters, may alternatively be utilized with the same or similar therapeutic effects.

As mentioned previously, the apparatus 10 allows for the creation of a closed ecological system in accordance with the above, thereby creating an environment conducive to the manufacture of exceptional pharmaceuticals for treating diseases and ailments for which safe and effective pharmaceuticals have not yet been discovered. Such exceptional pharmaceuticals may be obtained through natural organic production of living systems themselves or may be obtained by mixing various chemicals. For example, referring now to FIGS. 9 and 10, there can be seen a scanning electron microscope view of snake venom obtained from a Copperhead snake living under ordinary conditions found on earth (FIG. 9) and a scanning electron microscope view of snake venom obtained from the same snake, after the snake lived in an apparatus 10 housing a closed ecological system as is set forth above. Those skilled in the art will recognize the markedly improved characteristics of the venom shown in FIG. 10 obtained from the Copperhead snake that inhabited the closed ecological system of the present apparatus 10 for four weeks. Snake venom shown in FIG. 10 has been experimented with and found to have medicinal properties such as decreasing the size and occurrence of cancerous tumors, and providing relief from emotional illnesses. It is theorized that the toxicity of snake venom in the present invention would be lowered, if not eliminated, and the coherent structured chemical formation as shown would lead to immediate assimilation into patient receptors.

Those skilled in the art will recognize that the apparatus 10 may further comprise conveniences and necessaries to sustain life such as water nutrients, waste facilities and the like. Also, while the foregoing description has set forth the preferred embodiment of the invention in particular detail, it must be understood that numerous modifications, substitutions, and changes may be undertaken without departing from the true spirit and scope of the present invention as defined by the ensuing claims.

What is claimed is:

1. A method for establishing and maintaining a closed ecological system and atmosphere in a substantially hollow closed chamber comprising the steps of:
   a) providing a substantially hollow, closed, air-tight chamber to contain an atmosphere;
   b) introducing oxygen into said air-tight chamber to establish a concentration of oxygen within said air-tight chamber, said concentration ranging from approximately 22% to approximately 30% by volume of said atmosphere within said chamber, and maintaining said concentration of oxygen for a period of time;
   c) introducing carbon dioxide into said air-tight chamber to establish a concentration of carbon dioxide within said air-tight chamber said concentration of carbon dioxide ranging from 0.1% to 0.3% by volume of said atmosphere within said chamber, and maintaining said concentration of carbon dioxide for a period of time;
   d) elevating the atmospheric pressure within said air-tight chamber said atmospheric pressure ranging from one atmosphere to two atmospheres, and maintaining said atmospheric pressure for a period of time;
   e) providing means for establishing a magnetic field essentially throughout said chamber and maintaining said magnetic field for a period of time;
   f) maintaining a humidity in the range of 40% to 60% within said chamber;
   g) filtering any oxygen containing gas introduced into said chamber to remove airborne contaminants including dust and bacteria; and
   h) introducing at least one living organism into said chamber and maintaining said living organism in said chamber while said chamber is closed.

2. The method as recited in claim 1, wherein said magnetic field established within said chamber has a magnitude of 1 to 5 Gauss and a frequency in the range of approximately 0.5 Hz to approximately 30 Hz.

3. The method as recited in claim 1, further comprising the step of providing a predetermined wavelength of light within said chamber.

4. The method as recited in claim 3, wherein said light has a wavelength of approximately 6365 Angstroms.

5. The method as recited in claim 1, further comprising the step of broadcasting sounds within said chamber at a predetermined volume and frequency.

6. The method as recited in claim 5, wherein said sounds are bird songs broadcast into said chamber at a frequency of approximately 256 Hz ranging from 2–60 decibels in intensity.

7. The method as recited in claim 1, wherein said temperature within said chamber is maintained in the range of 70° F.–80° F.

8. The method as recited in claim 1, wherein said step of providing means for establishing a magnetic field essentially throughout said chamber is carried out by substantially surrounding said chamber with a magnetic field coil.

9. Apparatus for establishing and maintaining a closed ecological system having a controlled environment and capable of sustaining life over time, said apparatus comprising:

a closed, air tight, substantially hollowed chamber including at least one sealable access opening;

a closure member for closing said opening, said closure member when closed providing air tight closure;

means for maintaining a desired elevated pressure greater than one atmosphere in said chamber, said means for maintaining said desired elevated pressure including a pressure sensor coupled to a pressure control mechanism for controlling and regulating the pressure inside said chamber, a high pressure switch to prevent over pressurization of said chamber, and a low pressure switch to prevent under pressurization of said chamber;

an oxygen supply and control mechanism for supplying oxygen to said chamber and maintaining a predetermined oxygen concentration of 22% to 30% of volume therein;

a carbon dioxide supply and control mechanism for supplying carbon dioxide to said chamber and maintaining a carbon dioxide concentration in the range of 0.1% to 0.3% by volume therein;

means for regulating the temperature within said chamber;

humidity control means for controlling the humidity of said atmosphere within said chamber;

an air filtration system for filtering contaminants from the atmosphere found within said chamber; and means for establishing and maintaining a magnetic field within and substantially throughout said chamber.

10. An apparatus as recited in claim 9, wherein said oxygen supply and control mechanism and the carbon dioxide supply and control mechanism each comprises a valve assembly, a sensor in said chamber to detect the concentration of oxygen or carbon dioxide, respectively, within said chamber, and a control mechanism, respectively coupled to said sensor and said valve assembly for automatically opening and closing said valve assembly in response to the concentration of oxygen or carbon dioxide respectively detected in said chamber by each of said sensors.

11. An apparatus as recited in claim 10, wherein said valve assembly is a solenoid valve.

12. An apparatus as recited in claim 10, wherein said control mechanism is a digital computer.

13. An apparatus as recited in claim 9, wherein said means for establishing a magnetic field within and substantially throughout said chamber is provided by a magnetic field coil substantially surrounding at least a portion of said chamber.

14. An apparatus as recited in claim 9, wherein said magnetic field coil is connected to a power generator for generating a controlled electromagnetic pulses at energy levels in the range of 1 to 5 Gauss and at a frequency in the range of approximately 0.5 Hz to approximately 30 Hz.

15. An apparatus as recited in claim 9, wherein said magnetic field coil comprises copper wire and said power generator is coupled to a control mechanism for varying the magnitude and the direction of an electrical current flowing through said wire.

16. An apparatus as recited in claim 9, wherein said means for maintaining desired pressure within said chamber comprises a vacuum/pressure pump in fluid communication with said chamber to add or remove pressure from said chamber, and wherein further said apparatus further comprises a pressure control mechanism connected to said vacuum/pressure pump for selectively energizing said pump, and a pressure transducer in said chamber to detect the atmospheric pressure within said chamber, said pressure transducer connected to said a control mechanism to generate electrical signals depending upon the atmospheric pressure detected by said transducer such that said control mechanism automatically regulates the operation of said vacuum/pressure pump in response to said signals received from said transducer.

17. An apparatus as recited in claim 9, wherein said temperature regulating means comprises a heating and cooling pump provided in fluid communication with said chamber.

18. An apparatus as recited in claim 9, wherein said humidity control means comprises a humidity control unit in fluid communication with said chamber and a humidity sensor connected to said control unit, said sensor located within said chamber to detect the level of humidity in said chamber and to transmit electrical signals to said humidity control unit wherein said signals represent the level of humidity within said chamber.

19. An apparatus as recited in claim 18, wherein said humidity control unit is a gravity collection/injection valve mechanism.

20. An apparatus as recited in claim 9, further comprising lighting means for regulating the level of light found within chamber.

21. An apparatus as recited in claim 20, wherein said chamber includes at least one window formed therein and said lighting means comprises at least one light positioned adjacent to said window outside of said chamber for shining light into said chamber through said window.

22. An apparatus as recited in claim 21, wherein said at least one light is capable of producing magenta colored light having a wavelength of approximately 6365 Angstroms.

23. An apparatus as recited in claim 9, further comprising a sound system for broadcasting sounds within said chamber.

24. An apparatus as recited in claim 23, wherein said sound system includes a microphone located within said chamber for transmitting schemes from within said chamber to be broadcast outside of said chamber.

25. The apparatus to establish and contain a closed ecological system as recited in claim 9, wherein said closed substantially hollow chamber is in fluid communication with a sub-chamber through at least one conduit, said sub-chamber comprising at least one exterior portal selectively open to the ambient atmosphere and at least one communication portal selectively in said fluid communication with said closed substantially hollow chamber.

26. The apparatus for establishing and maintaining a closed ecological system as recited in claim 9, wherein said elevated pressure is maintained in excess of one atmosphere of pressure for essentially the entire treatment cycle of a living being.

27. The apparatus for establishing and maintaining a closed ecological system as recited in claim 9, wherein said elevated pressure, oxygen concentration, carbon dioxide concentration and magnetic field is essentially maintained during the entire treatment cycle of a living being.

28. The apparatus for establishing and maintaining a closed ecological system as recited in claim 9, wherein said chamber further comprises a satellite chamber fluidly connected to said closed hollow chamber, said fluid connection to said closed hollow chamber being selectively and temporarily severable to allow access to the interior of said satellite chamber without affecting said controlled environment of said closed hollow chamber.

* * * * *